US00PP32995P2

(12) United States Plant Patent
Heuger

(10) Patent No.: US PP32,995 P2
(45) Date of Patent: Apr. 20, 2021

(54) ***HELLEBORUS* PLANT NAMED 'COSEH 7700'**

(50) Latin Name: ***Helleborus* x *ericsmithii* X *Helleborus niger***
Varietal Denomination: COSEH 7700

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/873,652

(22) Filed: May 27, 2020

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. Anne Whealy

(57) ABSTRACT

A new and distinct cultivar of *Helleborus* plant named 'COSEH 7700', characterized by its upright to somewhat outwardly spreading and mounded plant habit; moderately vigorous to vigorous growth habit; dark green-colored leaves; freely flowering habit; light yellow green to white-colored flowers; and good garden performance.

2 Drawing Sheets

Figure 1:
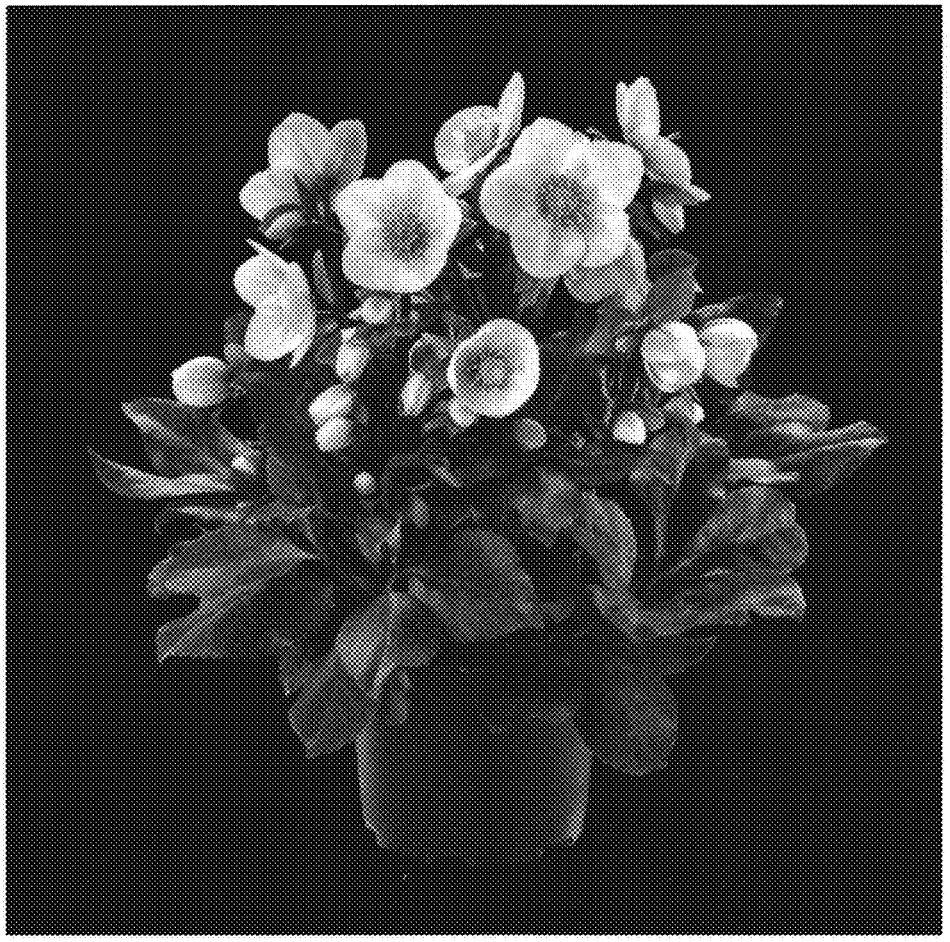

Botanical designation: *Helleborus* x *ericsmithii* X *Helleborus niger.*
Cultivar denomination: 'COSEH 7700'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1392. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *ericsmithii* X *Helleborus niger* and hereinafter referred to by the name 'COSEH 7700'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2011 of a proprietary selection of *Helleborus* x *ericsmithii* identified as code number P840, not patented, as the female, or seed patent and an unnamed selection of *Helleborus niger*, not patented, as the male, or pollen parent.

The new *Helleborus* plant was discovered and selected by the Inventor as a single flowering plant from within the progeny of the stated cross-pollination grown in a controlled greenhouse environment in Glandorf, Germany in December, 2013.

Asexual reproduction of the new *Helleborus* plant by in vitro axillary meristem culture in a controlled environment in Glandorf, Germany since March, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 7700'. These characteristics in combination distinguish 'COSEH 7700' as a new and distinct *Helleborus* plant:

1. Upright to somewhat outwardly spreading and mounded plant habit.
2. Moderately vigorous to vigorous growth habit.
3. Dark green-colored leaves.
4. Freely flowering habit.
5. Light yellow green to white-colored flowers.
6. Good garden performance.

Plants of the new *Helleborus* differ from plants of the female parent selection in the following characteristics:

1. Plants of the new *Helleborus* are more vigorous than plants of the female parent selection.
2. Plants of the new *Helleborus* have larger flowers than plants of the female parent selection.

Plants of the new *Helleborus* differ from plants of the male parent selection in the following characteristics:

1. Plants of the new *Helleborus* are more vigorous than plants of the male parent selection.

2. Plants of the new *Helleborus* have larger flowers than plants of the male parent selection.

Plants of the new *Helleborus* can also be compared to plants of *Helleborus niger* 'HGC Jesco', not patented. In side-by-side comparisons, plants of the new *Helleborus* differ primarily from plants of 'HGC Jesco' in the following characteristics:

1. Plants of the new *Helleborus* are more vigorous than plants of 'HGC Jesco'.
2. Plants of the new *Helleborus* have larger flowers than plants of 'HGC Jesco'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 7700' grown in a container.

Figure 2:
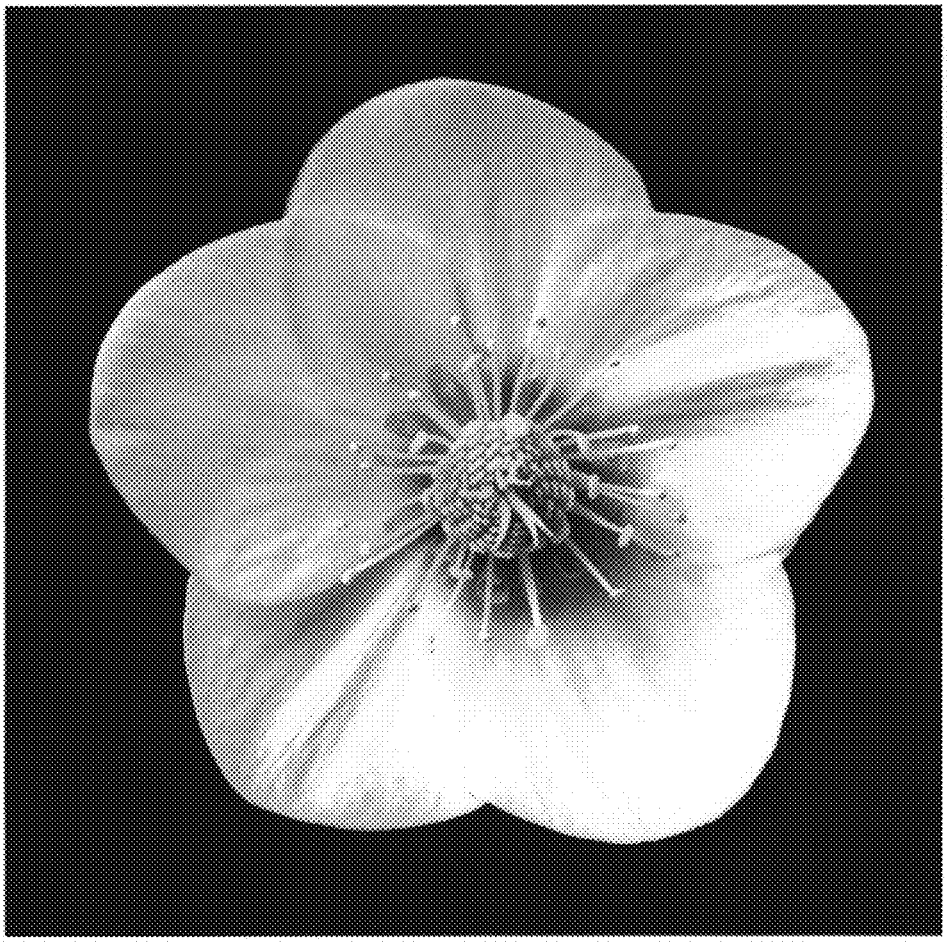

The photograph on the second sheet (FIG. 2 of 2) is a close-up view of a typical flower of 'COSEH 7700'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus niger* 'COSEH 7700'.

Parentage:

*Female, or seed, parent*.—Proprietary selection of *Helleborus* x *ericsmithii* disclosed as code number P840, not patented.

*Male, or pollen, parent*.—Unnamed selection of *Helleborus niger*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held within and above the foliar plane; plant shape, broadly ovate; moderately vigorous to vigorous growth habit and moderate to rapid growth rate.

*Plant height, soil level to top of foliar plane*.—About 28.1 cm.

*Plant height, soil level to top of flowers*.—About 41.9 cm.

*Plant diameter* (*area of spread*).—About 55.9 cm.

Leaf description:

*Arrangement*.—Leaves arranged in a basal rosette; leaves palmately compound with typically five leaflets per leaf.

*Leaf length*.—About 17.5 cm.

*Leaf width*.—About 20.1 cm.

*Leaflet length*.—About 12.1 cm.

*Leaflet width*.—About 7.1 cm.

*Leaf shape*.—Palmate; reniform in outline.

*Leaflet shape*.—Obovate to broadly elliptic; about 50% of the lower leaves are cleft.

*Leaflet apex*.—Acute.

*Leaflet base*.—Attenuate.

*Leaflet margin*.—Coarsely dentate to serrate; moderately coarsely undulate.

*Leaflet texture and luster, upper and lower surfaces*.—Smooth, glabrous; leathery; slightly glossy.

*Leaflet venation pattern*.—Pinnate.

*Leaflet color*.—Developing leaflets, upper surface: Darker than NN137C; midvein proximally tinged with close to between N186C and 200A. Developing leaflets, lower surface: Close to between 147B and 191A; midvein, close to 186C. Fully developed leaflets, upper surface: Darker than between NN137A and 139A; venation, close to 144B and proximally, close to 186C. Fully developed leaflets, lower surface: Close to 147B; venation, close to 186C.

*Petioles*.—Length: About 19 cm. Diameter: About 7 mm to 9 mm. Strength: Strong. Texture and luster, upper and lower surfaces: Smooth, glabrous; moderately glossy. Color, upper and lower surfaces: Close to N186C heavily covered with fine dots, close to 145B.

Flower description:

*Flower shape and habit*.—Rotate flowers; flowers slightly cupped; arranged in panicles; freely flowering habit with about three flowers per inflorescence and about 45 flowers developing per plant; flowers face mostly outwardly to slightly nodding.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 2 cm. Diameter: About 1 cm. Shape: Ovate. Texture and luster: Smooth, glabrous; matte. Color: Close to 157A.

*Inflorescence height* (*including peduncle*).—About 43.7 cm.

*Inflorescence diameter*.—About 17.7 cm.

*Flower diameter*.—About 7.9 cm by 7.9 cm.

*Flower depth* (*height*).—About 2.6 cm.

*Petals*.—All petals are transformed into nectaries.

*Sepals*.—Quantity and arrangement: About five or occasionally six, arranged in a single whorl. Length:

About 4.1 cm. Width: About 3.5 cm. Shape: Broadly ovate, slightly concave. Apex: Obtuse. Base: Broadly cuneate to truncate. Margin: Entire; moderately undulate. Texture and luster, upper surface: Smooth, glabrous; matte. Texture and luster, lower surface: Smooth, glabrous; slightly glossy. Color: When opening, upper surface: Close to between 150D and 155A; towards the margins, close to 155C; towards the base, close to 144B. When opening, lower surface: Close to between 150D and 155A occasionally flushed with close to 181D; towards the margins, close to 155C; towards the base, close to 146C. Fully opened, upper surface: Close to between 145D and 150D; towards the margins, close to between 150D and 155A; towards the base, close to 144A; venation, similar to lamina; with development becoming closer to 147C slightly tinged with close to 177B towards the margins and apex. Fully opened, lower surface: Close to 150D; towards the margins, close to 157B to 157C; towards the base, close to 144A; occasionally slightly flushed with close to 181D; venation, similar to lamina; with development becoming closer to between 148A and 197A and moderately tinged with close to 177A towards the margins and apex.

*Flower bracts*.—Quantity per flower: Typically one or two. Length: About 4.4 cm. Width: About 3.3 cm. Shape: Ovate. Apex: Bluntly acute to obtuse. Base: Truncate. Margin: Mostly entire; distally, slightly and finely serrate. Color, upper surface: Close to NN137A; midvein, slightly tinged with close to 183C. Color, lower surface: Close to between 147A and 148A; venation, close to N186C.

*Peduncles*.—Length: About 29.7 cm. Diameter: About 1.1 cm. Aspect: About 15° from vertical. Strength: Strong. Texture and luster: Smooth, glabrous; moderately glossy. Color: Close to 144C, heavily covered with fine dots and stripes, close to 183A to 183B.

*Pedicels*.—Length: About 1.8 cm. Diameter: About 3 mm. Aspect: About 10° to 20° from peduncle axis. Strength: Moderately strong. Texture and luster: Smooth, glabrous; slightly glossy. Color: Close to 152B to 152C moderately covered with fine dots, close to 178B.

*Reproductive organs*.—Stamens: Quantity per flower: About 70. Filament length: About 1.6 cm. Filament color: Close to 157D. Anther shape: Double and broadly reniform; basifixed. Anther size: About 2 mm by 2 mm. Anther color: Close to between 150C and 150D. Pollen amount: Sparse to moderate. Pollen color: Lighter than 4D. Pistils: Quantity per flower: About five to eight. Pistil length: About 1.1 cm. Stigma diameter: About 0.3 mm. Stigma shape: Club-shaped. Stigma color: Lighter than 150D. Style length: About 1 cm. Style color: Close to 157A to 157B. Ovary color: Close to 145B. Nectaries (transformed petals): Quantity per flower: About 12 to 16. Length: About 1.4 cm. Diameter: About 3 mm. Shape: Tubular, slightly flattened. Texture and luster, inner and outer surfaces: Smooth, glabrous; slightly glossy. Color, immature, inner and outer surfaces: Close to 144C; towards the apex, close to 7B. Color, mature, inner surface: Close to 144B; towards the apex, close to 7A; venation, similar to lamina; with development, becoming closer to 144A to 144B and towards the apex, close to 7A. Color, mature, outer surface: Close to 144B; towards the apex, close to 7A; towards the base, close to 146C; venation, similar to lamina; with development, becoming closer to 144A to 144B, towards the apex, close to 7A and towards the base, close to 146C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 7700' as illustrated and described.

* * * * *